US012781263B2

(12) United States Patent
Tadenuma et al.

(10) Patent No.: US 12,781,263 B2
(45) Date of Patent: Nov. 3, 2026

(54) NUCLEIC ACID SEQUENCE MEASUREMENT METHOD

(71) Applicant: Yokogawa Electric Corporation, Tokyo (JP)

(72) Inventors: Takashi Tadenuma, Musashino (JP); Yuki Miyauchi, Musashino (JP); Tomoyuki Taguchi, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 619 days.

(21) Appl. No.: 18/271,548

(22) PCT Filed: Jan. 14, 2022

(86) PCT No.: PCT/JP2022/001244
§ 371 (c)(1),
(2) Date: Jul. 10, 2023

(87) PCT Pub. No.: WO2022/158402
PCT Pub. Date: Jul. 28, 2022

(65) Prior Publication Data
US 2024/0068014 A1 Feb. 29, 2024

(30) Foreign Application Priority Data
Jan. 25, 2021 (JP) ................................ 2021-009830

(51) Int. Cl.
*C12Q 1/6816* (2018.01)
*C12Q 1/6806* (2018.01)
(Continued)

(52) U.S. Cl.
CPC ......... *C12Q 1/6816* (2013.01); *C12Q 1/6806* (2013.01); *C12Q 1/6837* (2013.01); *G01N 21/6428* (2013.01); *G01N 2021/6432* (2013.01)

(58) Field of Classification Search
None
See application file for complete search history.

(56) References Cited

U.S. PATENT DOCUMENTS

2012/0197008 A1 8/2012 Ozeki et al.
2014/0087388 A1 3/2014 Zhong
2015/0065377 A1 3/2015 Tadenuma et al.

FOREIGN PATENT DOCUMENTS

EP 2843059 A1 3/2015
EP 2481791 B1 5/2015
(Continued)

OTHER PUBLICATIONS

Extended European Search Report (EESR) dated Apr. 11, 2025 for European Patent Application No. 22742524.6.

*Primary Examiner* — Lore R Jarrett
(74) *Attorney, Agent, or Firm* — RANKIN, HILL & CLARK LLP

(57) ABSTRACT

A nucleic acid sequence measurement method for measuring a target RNA having a specific nucleic acid sequence included in a cell suspension by hybridization, including a step of heating the cell suspension at 100° C. to 200° C. in a pressurized state to obtain an RNA extract, a step of adding a proteolytic enzyme to the RNA extract to cause the RNA extract to be reacted, thereby preparing a sample solution, a step of supplying the sample solution to a device for nucleic acid sequence measurement, the device being equipped with a fluorescent probe that hybridizes with the target RNA, a step of subjecting the target RNA and the fluorescent probe to a hybridization reaction, and a step of measuring fluorescence from the device for nucleic acid sequence measurement.

5 Claims, 5 Drawing Sheets

(51) Int. Cl.

| | |
|---|---|
| ***C12Q 1/6837*** | (2018.01) |
| ***G01N 21/64*** | (2006.01) |

(56) References Cited

FOREIGN PATENT DOCUMENTS

| | | | |
|---|---|---|---|
| JP | 2012-157265 | A | 8/2012 |
| JP | 2014-512190 | A | 5/2014 |
| JP | 2015-43702 | A | 3/2015 |
| WO | 2019043779 | A1 | 3/2019 |

NUCLEIC ACID SEQUENCE MEASUREMENT METHOD

TECHNICAL FIELD

The present invention relates to a nucleic acid sequence measurement method.

BACKGROUND ART

As a method for measuring a target having a specific nucleic acid sequence included in a sample, a method using a DNA microarray (in which a detection probe having a sequence complementary to a specific nucleic acid sequence is provided on a solid-phase surface of a substrate or the like) is widely known. This method measures a target by utilizing a property whereby a target included in a sample added to a DNA microarray is captured by a detection probe of the DNA microarray by a hybridization reaction. In this method, the amount of the target included in the sample can be measured, in addition to determination of whether the target is included in the sample. Patent Document 1 discloses a measurement method for measuring a target using a DNA microarray.

In order to apply a target to a DNA microarray, it is necessary to extract a target nucleic acid. With regard to a case where the target is a nucleic acid included in a microorganism such as bacteria, a method is known for extracting the nucleic acid, for example, by a technique of lysing a cell membrane and the like of the microorganism through an enzymatic or chemical treatment, or by disrupting and the like through a physical stimulation using French Press, BeadBeater, or the like. In addition, Patent Document 2 discloses a method for extracting a nucleic acid by performing heating at a high temperature using a sealed container without using an enzymatic or chemical treatment or a physical treatment.

CITATION LIST

Patent Documents

[Patent Document 1]
Japanese Unexamined Patent Application, First Publication No. 2015-43702
[Patent Document 2]
Japanese Unexamined Patent Application, First Publication No. 2012-157265

DISCLOSURE OF INVENTION

Technical Problem

In the nucleic acid sequence measurement method in Patent Document 1, it is also conceivable that in a case where a sample including an extracted target (RNA) can be measured as it is without any treatment, labor and time required for measurement of the target can be significantly reduced. However, in a case where a sample including a target is directly applied to the nucleic acid sequence measurement method in Patent Document 1, there is a problem in that contaminants such as protein included in the sample may affect the hybridization reaction, resulting in the deterioration of measurement accuracy. In addition, the sample solution may become cloudy, making it impossible to detect fluorescence emitted from a DNA microarray. Moreover, during the fluorescence measurement, the protein contaminant (hereinafter also referred to as a contaminant protein) is excited by excitation light to exhibit fluorescence, raising a problem in that background light is caused to increase.

The present invention has been made in view of the above circumstances, and has an object to provide a nucleic acid sequence measurement method making it possible to measure an RNA having a specific sequence included in a sample solution with high accuracy while reducing labor and time required for the measurement.

Solution to Problem

In order to accomplish the object, the present invention adopts the following configurations.

[1] A nucleic acid sequence measurement method for measuring a target RNA having a specific nucleic acid sequence included in a cell suspension by hybridization, including:

a step of heating the cell suspension at 100° C. to 200° C. in a pressurized state to obtain an RNA extract;

a step of adding a proteolytic enzyme to the RNA extract to cause the RNA extract to be reacted, thereby preparing a sample solution;

a step of supplying the sample solution to a device for nucleic acid sequence measurement, the device being equipped with a fluorescent probe that hybridizes with the target RNA;

a step of subjecting the target RNA and the fluorescent probe to a hybridization reaction; and a step of measuring fluorescence from the device for nucleic acid sequence measurement.

[2] The nucleic acid sequence measurement method as described in [1], in which in the step of measuring the fluorescence, the fluorescence from the device for nucleic acid sequence measurement is measured without washing the sample solution supplied to the device for nucleic acid sequence measurement.

[3] The nucleic acid sequence measurement method as described in [1] or [2], in which in the step of obtaining the RNA extract, the cell suspension is heated in a sealed container.

[4] The nucleic acid sequence measurement method as described in any one of [1] to [3], in which the proteolytic enzyme is a proteinase K.

[5] The nucleic acid sequence measurement method as described in any one of [1] to [4], in which the device for nucleic acid sequence measurement is equipped with a fluorescent probe having a binding part and a proximal end, and having a fluorescent molecule attached to a distal end or an intermediate position, a quenching probe having a binding part and a proximal end, and having a quenching molecule attached to a position near the fluorescent molecule of the fluorescent probe in a case where the quenching probe binds to the fluorescent probe, and a substrate having a solid-phase surface on which each of the proximal end of the fluorescent probe and the proximal end of the quenching probe is immobilized, the binding part of the fluorescent probe and the binding part of the quenching probe have sequences complementary to each other, at least one of the fluorescent probe and the quenching probe has a detection part having a sequence complementary to a nucleic acid sequence of the target RNA, in a case where a hybridization between the target RNA and the detection part does not occur, binding between the binding part of the fluorescent probe and the binding part of the quenching probe is maintained, and fluorescence exhibited by the fluorescent molecule is consequently quenched by the quenching molecule approaching the fluorescent molecule, and in a case where the hybridization between the target RNA and the detection part occurs, the binding between the binding part of the fluorescent probe and the binding part of the quenching probe is consequently dissociated, and the proximal end of each of the fluorescent probe and the quenching probe is immobilized on the solid-phase surface to cause a positional relationship so that the fluorescent molecule separated from the quenching molecule exhibits fluorescence.

Advantageous Effects of Invention

According to the nucleic acid sequence measurement method of the present invention, there is an effect such that an RNA having a specific sequence included in a sample solution can be measured with high accuracy while reducing labor and time required for the measurement.

BEST MODE FOR CARRYING OUT THE INVENTION

Figure 1:
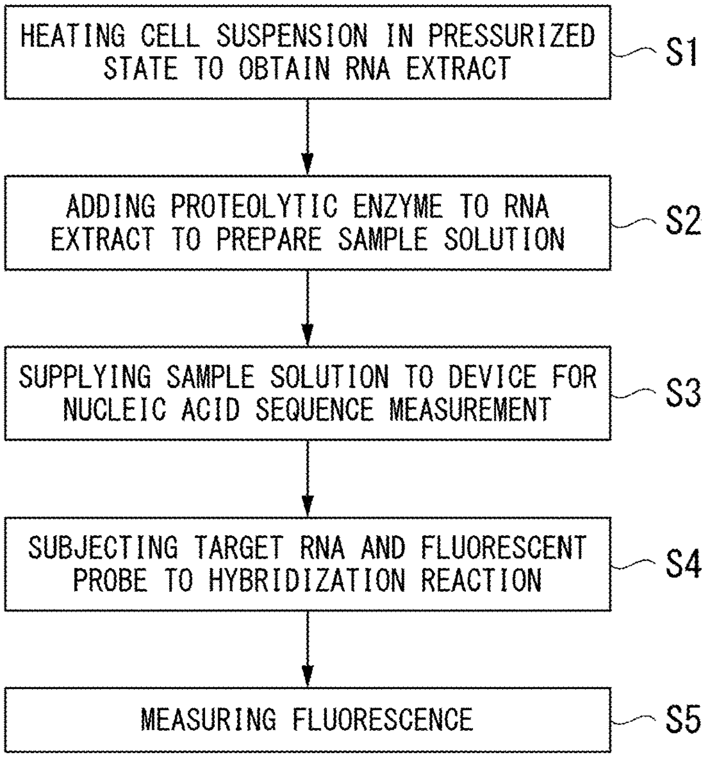
FIG. 1 is a flow chart showing an example of the nucleic acid sequence measurement method of the present invention.

Hereinafter, the nucleic acid sequence measurement method according to an embodiment of the present invention will be described in detail with reference to the drawings. Hereinbelow, a summary of the embodiments of the present invention will first be described, and then details of the embodiments of the present invention will be described.

SUMMARY

The embodiments of the present invention make it possible to measure an RNA having a specific sequence included in a sample solution with high accuracy while reducing labor and time required for the measurement. In the method disclosed in the above-mentioned Patent Document 1, a target is measured using a device (DNA microarray) for nucleic acid sequence measurement, the device being provided with, as a detection probe, a fluorescent probe to which a fluorescent molecule has been attached and a quenching probe to which a quenching molecule for quenching the fluorescence of the fluorescent molecule has been attached. This method makes it possible to measure the target without attaching the fluorescent molecule to the target and without washing the DNA microarray (washing to remove uncaptured targets and the like).

In this method, in a case where a target is not present in a device for nucleic acid sequence measurement, which determines the presence or absence or measures the amount of a specific nucleic acid using the DNA microarray, the binding of a fluorescent probe and a quenching probe, which are independent of each other, through a binding part is maintained. Thus, fluorescence of the fluorescent molecule is quenched by the quenching molecule. In a case where a target is supplied, the target binds to a detection part, the binding between the fluorescent probe and the quenching probe through the binding part is dissociated, and separation of the quenching molecule from the fluorescent molecule causes the fluorescent molecule to emit fluorescence. A target included in a sample can be measured by using this device for nucleic acid sequence measurement.

The nucleic acid extraction method disclosed in the above-mentioned Patent Document 2 is a nucleic acid extraction method including a step of introducing a cell suspension into a container, a step of sealing the container, and a step of heating the cell suspension accommodated in the container to a specified maximum temperature of 100° C. or higher in the state where the container is sealed.

However, in a case where a sample including a target is directly applied to the nucleic acid sequence measurement method in Patent Document 1, there is a problem in that contaminants such as protein included in the sample may affect the hybridization reaction, resulting in deterioration of a measurement accuracy. In addition, the sample solution may become cloudy, making it impossible to detect fluorescence emitted from the DNA microarray. Moreover, during the fluorescence measurement, the contaminant protein is excited by excitation light, exhibiting fluorescence, which raises a problem in that background light is increased.

Embodiments

The nucleic acid sequence measurement method of the present embodiment is a nucleic acid sequence measurement method for measuring a target RNA having a specific nucleic acid sequence included in a cell suspension by hybridization, including a step of heating the cell suspension at 100° C. to 200° C. in a pressurized state to obtain an RNA extract, a step of adding a proteolytic enzyme to the RNA extract to cause the RNA extract to be reacted, thereby preparing a sample solution, a step of supplying the sample solution to a device for nucleic acid sequence measurement, the device being equipped with a fluorescent probe that hybridizes with the target RNA, a step of subjecting the target RNA and the fluorescent probe to a hybridization reaction, and a step of measuring fluorescence from the device for nucleic acid sequence measurement. This makes it possible to suppress an influence of the contaminant protein and measure the target RNA included in the sample solution with high accuracy while reducing labor and time required for the measurement. In addition, it is possible to prevent the sample solution from becoming cloudy and lowering fluorescence intensity during the hybridization reaction. Moreover, background light due to the contaminant protein can be reduced.

Hereinafter, the nucleic acid sequence measurement method of the present embodiment will be described. FIG. 1 is a flow chart showing an example of the nucleic acid sequence measurement method of the present invention. The nucleic acid sequence measurement method of the present invention will be described below with reference to FIG. 1.

First, a cell suspension is heated at 100° C. to 200° C. under pressure to obtain an RNA extract (step S1). A cell from which an RNA is to be extracted is not particularly limited, and examples thereof include microbial cells.

Examples of microorganisms include *Acinetobacter* species, *Actinomyces* species, *Aerococcus* species, *Aeromonas* species, *Alclaigenes* species, *Bacillus* species, *Bacteriodes* species, *Bordetella* species, *Branhamella* species, *Brevibacterium* species, *Campylobacter* species, *Candida* species, *Capnocytophagia* species, *Chromobacterium* species, *Clostridium* species, *Corynebacterium* species, *Cryptococcus* species, *Deinococcus* species, *Enterococcus* species, *Erysielothrix* species, *Escherichia* species, *Flavobacterium* species, *Gemella* species, *Haemophilus* species, *Klebsiella* species, *Lactobacillus* species, *Lactococcus* species, *Legionella* species, *Leuconostoc* species, *Listeria* species, *Micrococcus* species, *Mycobacterium* species, *Neisseria* species, *Cryptosporidium* species, *Nocardia* species, *Oerskovia* species, *Paracoccus* species, *Pediococcus* species, *Peptostreptococcus* species, *Propionibacterium* species, *Proteus* species, *Pseudomonas* species, *Rahnella* species, *Rhodococcus* species, *Rhodospirillium* species, *Staphlococcus* species, *Streptomyces* species, *Streptococcus* species, *Vibrio* species, and *Yersinia* species. The present invention can also be applied to animal cells, insect cells, plant cells, mycoplasma, viruses, and the like other than the microorganisms. The cells in the present invention may exist together with a plurality of different types of cells as described above. In addition, there are microorganisms that take forms of bacterial spores or fungal spores in an oligotrophic state, but the cell state due to such a growth state is irrelevant.

The cell suspension is obtained by suspending cells in a culture solution, a buffer solution, or the like. The cell suspension may be either a cell culture solution or a suspension obtained by suspending the cell culture solution in a buffer. Here, the buffer solution is one used for stabilization, efficiency, and the like of RNA extraction, and for example, a Tris-HCl buffer solution, a phosphate buffer solution, a sodium borate buffer solution, a saline sodium citrate buffer solution (SSC buffer solution), a saline sodium phosphate-EDTA buffer solution (SSPE buffer solution), a carbonate-bicarbonate buffer solution, or the like is used.

Next, the cell suspension is heated at 100° C. to 200° C. under pressure to obtain an RNA extract. A method for heating the cell suspension at 100° C. to 200° C. under pressure is not particularly limited as long as the cell suspension can be heated to 100° C. to 200° C. at a pressure higher than atmospheric pressure, and examples of the method include a method in which a cell suspension is accommodated in a container, and the container is sealed, and heated at 100° C. to 200° C. The heating temperature only needs to be 100° C. to 200° C., which is appropriately determined depending on the type of cell to be applied, but is preferably 120° C. to 165° C., more preferably 120° C. to 160° C., and particularly preferably 140° C. to 160° C. By setting the heating temperature to 100° C. to 200° C., the target RNA can be uniform and have a suitable fragment length. In a case where the heating temperature is lower than 100° C., the efficiency of extracting the target RNA from the cell may decrease. In addition, the target RNA fragment may be too long to bind to the fluorescent probe. Moreover, in a case where the heating temperature is higher than 200° C., the fragment length of the target RNA is too short and the efficiency of hybridization to the fluorescent probe may decrease.

The pressurized state is not particularly limited as long as it is at least atmospheric pressure, but is preferably 100 to 1,500 kPa, and more preferably 200 to 700 kPa. By setting the pressure to 100 to 1,500 kPa, the target RNA can be more uniform and have a suitable fragment length. In a case where the pressure is less than 100 kPa, the efficiency of extracting the target RNA from the cell may decrease. In addition, the target RNA fragment may be too long to bind to the fluorescent probe. On the other hand, in a case where the pressure is more than 1,500 kPa, the fragment length of the target RNA is too short, and the efficiency of hybridization to the fluorescent probe may decrease.

A container for accommodating the cell suspension is not particularly limited as long as it has a mechanical structure for sealing and has heat resistance, and examples thereof include a boil lock type tube, a heat-resistant resin tube, a metal container, and a glass container. The means for heating is not particularly limited as long as it can be heated to 100° C. to 200° C., and examples thereof include dry heat block, oil bath, microwave, direct flame heating, and steam heating.

The heating time is not particularly limited and can be appropriately set depending on the type of cell to be applied, the amount of cell suspension, and the like, but the heating time is preferably 20 seconds to 10 minutes, and more preferably 30 seconds to 5 minutes, and may be, for example, 40 seconds to 3 minutes, 1 to 2 minutes, or the like.

For example, in a case where the cell is a microbial cell, an example of heating conditions suitable for Gram-negative bacteria can be a condition in which the heating time is 15 seconds or more and less than 2 minutes and the heating temperature is 105° C. to 125° C. or lower.

For example, in a case where the cell is a microbial cell, an example of heating conditions suitable for Gram-positive bacteria and fungi can be a condition in which the heating time is 1 minute or less and the heating temperature is 125° C. to 160° C. or lower.

In a case where a sealed container is used to cause a pressurized state, the volume of the container capable of uniformly heating the cell suspension in a short time is preferably 2 ml or less, more preferably 0.6 ml or less, and particularly preferably 0.2 ml or less.

The cell suspension may be cooled after the heating. As a cooling method after the heating, rapid cooling or natural cooling may be used. Examples of a method for the rapid cooling include a method of rapidly cooling the heated cell suspension together with the container using a Peltier element or the like. In a case where the cell suspension is subjected to rapid cooling, thermal shock occurs and the cell disrupting efficiency increases. Therefore, the efficiency of RNA extraction is improved. This method is effective for cells with rigid structures, such as Gram-positive bacteria and fungi.

Examples of a method for natural cooling include a method in which a container accommodating the heated cell suspension is allowed to stand at room temperature and cooled naturally. Since in a case where the cell suspension is naturally cooled, no thermal shock is applied, an RNA can be extracted in a state where damage to the RNA is suppressed. This method is effective in a case where a long-chain RNA is extracted.

After the heating, the cell suspension is released from the pressurized state. With regard to the release of the pressurized state, the pressurized state may be released while under pressure, or may be released after the pressurized state is reduced to atmospheric pressure. Examples of the method for releasing the pressurized state while under pressure include a method in which the sealed state of a container which is in a high-temperature state of 100° C. to 200° C. is released. In a case where the sealed state of the container which is in a high-temperature state of 100° C. to 200° C. is released, the internal pressure at the time of the release is higher than atmospheric pressure, and a sudden pressure change occurs. Therefore, a shearing force is generated, improving the cell disrupting efficiency, and thus, the RNA extraction efficiency can be improved. This method is effective for cells with rigid structures, such as Gram-positive bacteria and fungi.

Examples of a method for releasing the pressurized state after reducing the pressurized state to atmospheric pressure include a method in which a sealed state of a container is released after cooling the container in a high-temperature state of 100° C. to 200° C. to 100° C. or lower. In a case where the container in a high-temperature state of 100° C. to 200° C. is cooled to 100° C. or lower and then the sealed state of the container is released, no shearing force is applied at the time of the release. Therefore, an RNA can be extracted in the state where RNA damage is suppressed. This method is effective in a case where a long-chain RNA is extracted.

A cell lysis accelerator may be used in a case where an RNA is extracted from a cell suspension. By using the cell lysis accelerator, the RNA extraction can be efficiently performed for cells having a rigid structure, such as Gram-positive bacteria and fungi, and cells in a more rigid state, such as bacterial spores and oocysts. The addition of the cell lysis accelerator may be performed before high-temperature treatment or after the high-temperature treatment.

In a case where a cell lysis accelerator is added to a sample before high-temperature treatment, the cell membrane structure is weakened by the cell lysis accelerator, the high-temperature treatment works effectively, and the RNA extraction efficiency is improved. The high-temperature treatment in the cell lysis accelerator can exert the action effectively. This is effective in a case where the amount of sample is small and it is desired to perform the extraction more reliably under a single condition.

In a case where a cell lysis accelerator is added to a sample after high-temperature treatment, the cell membrane structure can be weakened by the high-temperature treatment and then the cell lysis accelerator can be allowed to act effectively, making it possible to extract a nucleic acid with high efficiency in a short time. This is effective for cells with rigid structures.

Examples of the cell lysis accelerator include alkalis (NaOH, KOH, and the like), acids (HCl, $H_2SO_4$, and the like), enzymes (proteolytic enzymes: a proteinase K and the like, polysaccharide decomposing enzymes: a chitinase, a lysozyme, a zymolyase, and the like), surfactants (anionic surfactants: SDS and the like, cationic surfactants: cetyltrimethylammonium bromide (CTAB) and the like, nonionic surfactants: Triton-X and the like, amphoteric surfactants: betaines (a generic name of compounds having specific structures, trimethylglycine and the like), and the like), redox agents (hydrogen peroxide, β-mercaptoethanol, dithiothreitol, and the like), protein denaturants (guanidine hydrochloride, urea, and the like), and chelating agents (ethylenediaminetetraacetic acid (EDTA) and the like). A plurality of these cell lysis accelerators may be mixed and used. A buffer solution may be added thereto as necessary.

In a case where a sealed container is used to create a pressurized state, it is possible to speed up the transition to a high-temperature pressurized state by controlling the state inside the container. Specifically, mention may be made of a method in which a cell suspension is introduced into a container so as not to leave air bubbles, an air layer, and the like, and the container is sealed and then transited to a heating step. In addition, the sealability can also be improved by layering a high-boiling-point solvent such as a mineral oil on the air layer of the cell suspension which is small relative to the internal volume of the container. Also in this case, the container is sealed and then heated. In this case, vapor fills the vapor phase portion to perform the heating to the boiling point or higher after reaching a saturated vapor pressure. For this reason, the inside of the container is pressurized more quickly and can thus reach a high temperature of 100° C. to 200° C.

In a case where a sealed container is used in order to create a pressurized state, the sealed state can be prevented from being released as the internal pressure of the container increases by mechanically sealing the container. This makes it possible to carry out heating treatment stably. Examples of the mechanical sealing include a method of performing pressing with a member having a shape that matches the container (fixed fittings).

Next, a proteolytic enzyme is added to the RNA extract to cause the RNA extract to be reacted, thereby preparing a sample solution (step S2). Here, the proteolytic enzyme is not particularly limited as long as it can decompose a cell-derived contaminant protein included in the RNA extract, and examples thereof include a proteinase K, an actinase E, a trypsin, a chymotrypsin, and a pepsin. These proteolytic enzymes may be used alone or in combination of a plurality of kinds thereof.

In this step, the cell-derived contaminant protein included in the RNA extract is decomposed by the proteolytic enzyme. Due to this, the influence of the contaminant protein is suppressed. In addition, the cloudiness of the sample solution due to a reaction between the contaminant protein and a salt used in a hybridization reaction in a device for nucleic acid sequence measurement described later is suppressed. Moreover, in the step of measuring fluorescence from the device for nucleic acid sequence measurement described later, the contaminant protein can be suppressed from being excited by excitation light to exhibit fluorescence, and thus, the background light can be reduced.

The amount of proteolytic enzyme added to the RNA extract is not particularly limited as long as it is an amount such that the cell-derived contaminant protein can be decomposed, and the amount is, for example, an amount such that the final concentration in the reaction solution is 20 to 500 μg/mL.

A reaction temperature between the contaminant protein in the RNA extract and the proteolytic enzyme is appropriately determined according to the optimum temperature of a proteolytic enzyme used, and for example, in a case of a proteinase K, the reaction temperature is 30° C. to 40° C. A reaction time is appropriately determined according to the properties of a proteolytic enzyme used, and for example, in a case of a proteinase K, the reaction time is 10 to 20 minutes.

Next, the sample solution is supplied to a device for nucleic acid sequence measurement equipped with a fluorescent probe that hybridizes with the target RNA (step S3). A salt is added to the sample solution in order to hybridize the target RNA having a specific nucleic acid sequence and the fluorescent probe. Examples of the salt to be added include sodium chloride. Instead of the salt, a buffer solution including a salt may be added. Examples of the buffer solution including a salt include an SSC buffer solution, a Church's phosphate buffer solution, and an SSPE buffer solution.

The concentration of the salt to be added is preferably, for example, a concentration which will provide a 2- to 10-fold diluted final concentration, and more preferably a concentration which will provide a 5-fold diluted final concentration.

Examples of the device for nucleic acid sequence measurement to which a sample solution is supplied include the device for nucleic acid sequence measurement disclosed in Japanese Unexamined Patent Application, First Publication No. 2015-43702.

Specifically, the device for nucleic acid sequence measurement is equipped with a fluorescent probe having a binding part and a proximal end, and having a fluorescent molecule attached to a distal end or an intermediate position, a quenching probe having a binding part and a proximal end, and having a quenching molecule attached to a position near the fluorescent molecule of the fluorescent probe in a case where the quenching probe binds to the fluorescent probe, and a substrate having a solid-phase surface on which the proximal end of each of the fluorescent probe and the quenching probe is immobilized, in which the binding part of the fluorescent probe and the binding part of the quenching probe have nucleic acid sequences complementary to each other, at least one of the fluorescent probe and the quenching probe has a detection part having a nucleic acid sequence complementary to a nucleic acid sequence of the target RNA, in a case where a hybridization between the target RNA and the detection part does not occur, binding between the binding part of the fluorescent probe and the binding part of the quenching probe is maintained, and fluorescence exhibited by the fluorescent molecule is consequently quenched by the quenching molecule approaching the fluorescent molecule, and in a case where the hybridization between the target RNA and the detection part occurs, the binding between the binding part of the fluorescent probe and the binding part of the quenching probe is dissociated consequently, and the proximal end of each of the fluorescent probe and the quenching probe is immobilized on the solid-phase surface to cause a positional relationship so that the fluorescent molecule separated from the quenching molecule exhibits fluorescence. Therefore, in a case where a hybridization between the target RNA and the detection part does not occur, binding between the binding part of the fluorescent probe and the binding part of the quenching probe is maintained. As a result, fluorescence exhibited by the fluorescent molecule is quenched by the quenching molecule approaching the fluorescent molecule. In a case where the hybridization between the target RNA and the detection part occurs, the binding between the binding part of the fluorescent probe and the binding part of the quenching probe is dissociated. As a result, the fluorescent molecule separated from the quenching molecule exhibits fluorescence.

According to this device for nucleic acid sequence measurement, the proximal ends of each of the fluorescent probe and the quenching probe, which are molecules independent of each other, are immobilized. Thus, the quenching effect can be appropriately exhibited and the detection sensitivity can be improved. In addition, a labeling step is not necessary, and it is also possible to omit a washing step.

Figure 2:
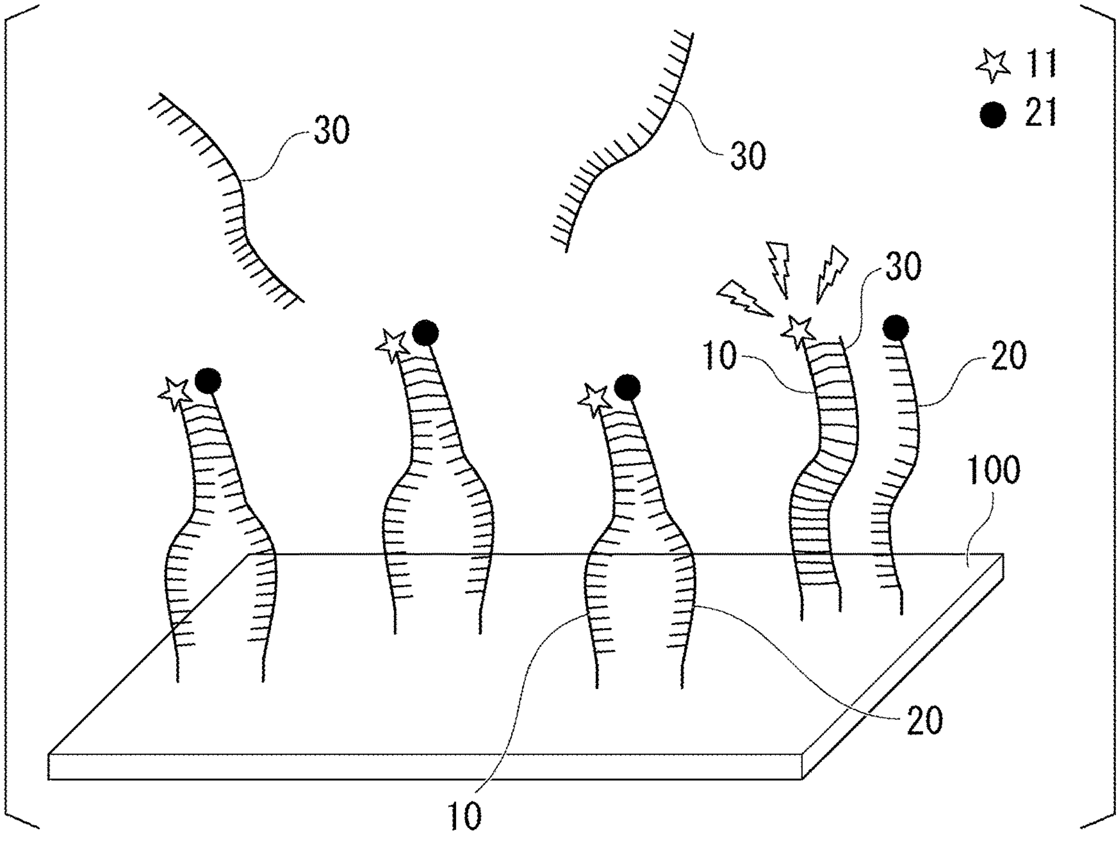
FIG. 2 is a view showing a configuration example of a device for nucleic acid sequence measurement used in the nucleic acid sequence measurement method of the present invention.
Figure 3:
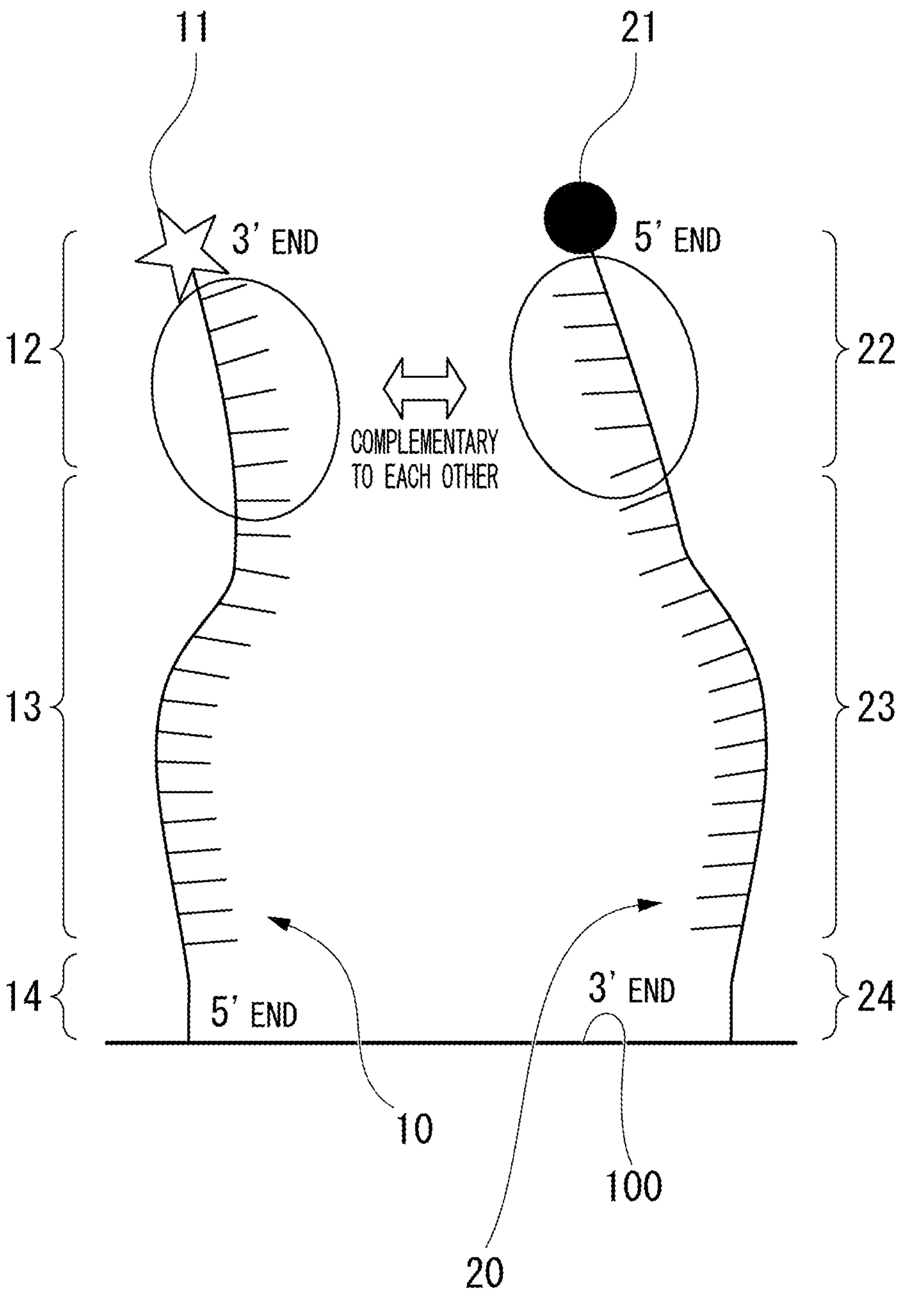
FIG. 3 is a view showing a configuration example of a probe.

FIG. 2 is a view showing a configuration example of a device for nucleic acid sequence measurement used in the nucleic acid sequence measurement method of the present invention, and FIG. 3 is a view showing a configuration example of a probe.

As shown in FIGS. 2 and 3, the device for nucleic acid sequence measurements has a fluorescent probe 10 having a fluorescent molecule 11 attached to a complementary sequence of a target RNA 30 to be detected and a quenching probe 20 having a quenching molecule 21 attached to the complementary sequence, in which the fluorescent probe 10 and the quenching probe 20 are each immobilized on a solid-phase surface 100 of a substrate or the like.

The present invention employs a principle of quenching through fluorescence resonance energy transfer.

The fluorescent molecule used in the present invention is not particularly limited as long as it is a molecule emitting fluorescence in a case of being excited by specific excitation light but, for example, known substances such as EDANS, Coumarin, FAM, FITC, Cy2, TF2, TF3, HEX, JOE, TET, Cy3, Cy5, Alexa Fluor (registered trademark) 532, Alexa Fluor (registered trademark) 610, Alexa Fluor (registered trademark) 647, ATTO532, ATTO633, Qdot (registered trademark) 565, Qdot (registered trademark) 585, Qdot (registered trademark) 605, Qdot (registered trademark) 705, iFluor™ 532, and iFluor™ 647 can be used.

The quenching molecule used in the present invention is not particularly limited but, for example, known substances such as Dabcyl, TQ1, TQ2, TQ3, Eclipse (registered trademark), BHQ1, BHQ2, BHQ3, Cy5Q, Cy7Q, lowa Black (registered trademark) FQ, lowa Black (registered trademark) RQ, IRDye QC-1, QSY7, QSY21, and QXL570 can be used.

A combination of the fluorescent molecule and the quenching molecule is also not particularly limited, but examples thereof include a combination of EDANS, Coumarin, or TF2 with Dabcyl or TQ1, a combination of FAM, FITC, TET, Alexa Fluor (registered trademark) 532, Cy2, Cy3, TF2, or TF3 with TQ2, a combination of Alexa Fluor (registered trademark) 532, Cy3, HEX, JOE, TF2, TF3, TF4, or TET with TQ3, a combination of Alexa Fluor (registered trademark) 532, TF2, Cy3, FAM, or HEX with Eclipse (registered trademark), a combination of Alexa Fluor (registered trademark) 532, TF2, TF3, Cy3, FAM, HEX, TET, or Cy3 with BHQ1, a combination of TF3, TF4, Cy3, Cy5, or HEX with BHQ2, a combination of Cy5, Alexa Fluor (registered trademark) 647, or TF5 with Iowa Black (registered Trademark) RQ, IRDye QC-1, QSY21, TQ4, TQ5, BHQ2, or BHQ3, a combination of Cy3, TF3, or TF4 with Cy5Q, Iowa Black (registered trademark) FQ, Iowa Black (registered trademark) RQ, IRDye QC-1, QSY7, or QXL570, a combination of Alexa Fluor (registered trademark) 532 with Cy5Q, TQ2, TQ3, Iowa Black (registered trademark) FQ, Iowa Black (registered trademark) RQ, IRDye QC-1, QSY7, or QXL570, and a combination of TF3 with BHQ1, BHQ2, or Cy5Q.

As the substrate used in the present invention, plate-shaped quartz having a rectangular shape as viewed from above, glass, silicon, single crystals such as calcium fluoride and sapphire, ceramics, resin materials, or the like can be used. Examples of the resin materials include a cycloolefin polymer (COP), a cyclic olefin copolymer (COC), a polycarbonate, an acrylic resin, and a polyethylene resin, each of which has excellent optical characteristics, and chemical and thermal stability. Furthermore, the shape of the substrate in a case of being viewed from above may be any shape.

As shown in FIG. 3, the fluorescent probe 10 is equipped with an X part 12 of a several-bases which is provided from the 3' end and serves as a complementary sequence of the target RNA 30, a detection sequence 13 which is provided following the X part 12 and serves as a complementary sequence of the target RNA 30, and a linker 14 which is connected to the detection sequence 13 and extended to the 5' end, and the fluorescent molecule 11 is immobilized at the 3' end of the fluorescent probe 10.

The quenching probe 20 is equipped with a Y part 22 of a several-bases which is provided from the 5' end, a detection sequence 23 which is provided following the Y part 22 and serves as a complementary sequence to the target RNA 30, and a linker 24 which is connected to the detection sequence 23 and extended to the 3' end, and the quenching molecule 21 is immobilized at the 5' end of the quenching probe 20.

The fluorescent probe 10 and the quenching probe 20 are immobilized on the solid-phase surface 100 through each of the linker 14 and the linker 24. In addition, the sequence of the X part 12 of the fluorescent probe 10 and the sequence of the Y part 22 of the quenching probe 20 are complementary to each other. Moreover, the fluorescent probe 10 and the quenching probe 20 are immobilized at positions where the X part 12 of the fluorescent probe 10 and the Y part 22 of the quenching probe 20 can bind to each other, and in a case where the X part 12 of the fluorescent probe 10 and the Y part 22 of the quenching probe 20 bind to each other, a positional relationship such that the quenching molecule 21 approaches the fluorescent molecule 11, thereby putting the fluorescent molecule 11 into a quenching state, is secured.

In addition, it is desirable to design the affinity between the fluorescent probe 10 and the target RNA 30 to be higher than the affinity between the fluorescent probe 10 and the quenching probe 20 through the X part 12 and the Y part 22.

Furthermore, in the present invention, the term, "complementary", means having nucleic acid sequences where one nucleic acid sequence and another nucleic acid sequence can form a double-stranded state, it is not necessary that the nucleic acid sequences are completely complementary, and several mismatched base pairs may be included.

In addition, the fluorescent molecule or the quenching molecule may not be attached to a distal end of the probe, or the fluorescent molecule or the quenching molecule may be attached at a position in the middle of the probe.

The device for nucleic acid sequence measurement used in the nucleic acid sequence measurement method of the present invention can be produced as follows.

(1) Preparation of Solution

First, a probe solution is prepared by mixing the fluorescent probe 10 and the quenching probe 20, and the probe concentration is adjusted.

(2) Coupling

Next, the probe solution is heated and then rapidly cooled to couple the fluorescent probe 10 and the quenching probe 20. Thus, the fluorescent probe 10 and the quenching probe 20 are bound to each other through the X part 12 and the Y part 22. Here, for example, after heating the probe solution to 95° C., the temperature is maintained for 5 minutes and then rapidly lowered to 25° C. to couple the fluorescent probe 10 and the quenching probe 20.

(3) Immobilization onto Solid-phase Surface

Next, the probe solution in which the fluorescent probe 10 and the quenching probe 20 are coupled is spotted on a solid-phase surface to immobilize the fluorescent probe 10 and the quenching probe 20 on the solid-phase surface 100.

(4) Washing

Next, the solid-phase surface 100 is washed to remove excess probes which are not immobilized. By the procedure above, a device for nucleic acid sequence measurement is produced.

Since the fluorescent probe 10 and the quenching probe 20 are bound to the solid-phase surface 100 in the state where they are bound to each other through the X part 12 and the Y part 22, the positional relationship between the fluorescent probe 10 and the quenching probe 20 can be appropriately managed and the quenching effect can be appropriately exerted. Therefore, the detection sensitivity can be improved.

Figure 4:
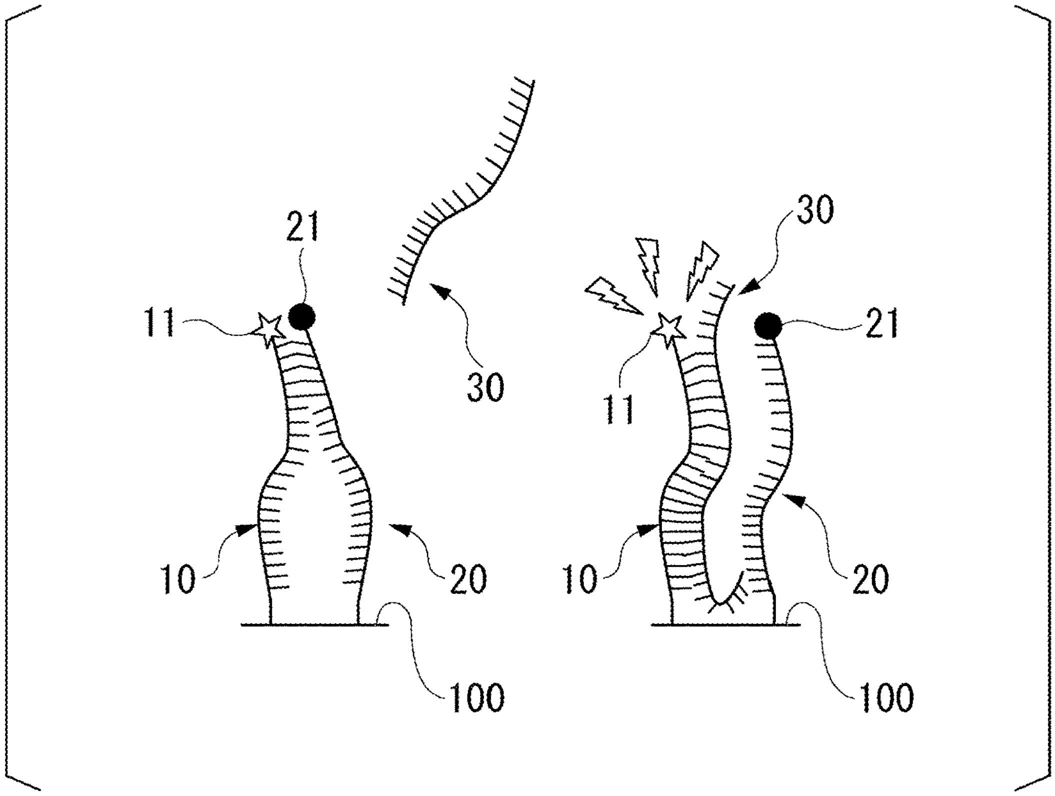
FIG. 4 is a view schematically showing the principle of detecting a target RNA.

Next, the target RNA 30 and the fluorescent probe 10 are subjected to a hybridization reaction (step S4). As shown in FIG. 4, in a case where the target RNA is not present, the X part 12 and the Y part 22 (FIG. 3) of several bases, each adjacent to the fluorescent molecule 11 and the quenching molecule 21, bind to each other, which causes a state where the fluorescent molecule 11 approaches the quenching molecule 21. In this state, the fluorescent molecule 11 does not exhibit fluorescence due to an influence of the quenching molecule 21 even with irradiation with excitation light.

In a case where a sample solution including the target RNA 30 is supplied to the solid-phase surface 100 of the device for nucleic acid sequence measurement and a hybridization reaction is performed, the target RNA 30 binds to the fluorescent probe 10 as shown in FIG. 4. As a result, the binding between the X part 12 and the Y part 22 is released and the distance between the quenching molecule 21 and the fluorescent molecule 11 is increased. Thus, the quenching state is released and the fluorescent molecule 11 is caused to emit fluorescence upon irradiation with excitation light.

Next, after the hybridization reaction, the fluorescence from the device for nucleic acid sequence measurement is measured (step S5). As described above, in a case where the target RNA 30 binds to the fluorescent probe 10 in the sample solution, the binding between the X part 12 and the Y part 22 is released, and the distance between the quenching molecule 21 and the fluorescent molecule 11 is increased. As a result, the quenching state of the fluorescent molecule 11 is released and the fluorescent molecule 11 emits fluorescence upon irradiation with excitation light. The presence or absence of the target RNA 30 in the sample solution can be confirmed by measuring this fluorescence with a fluorescence-reading apparatus described later. In addition, the target RNA 30 included in the sample solution can be quantified by measuring fluorescence intensity from the device for nucleic acid sequence measurement. Moreover, at this time, since the uncaptured target RNA 30 included in the solution does not exhibit fluorescence, the device for nucleic acid sequence measurement does not need to be washed. Therefore, it is possible to observe the solid-phase surface through the solution in the presence of the sample solution. According to the present invention, it is possible to suppress the cloudiness of the sample solution due to a reaction between contaminant protein and the salt used in a hybridization reaction, and to reduce background light caused by the contaminant protein. Therefore, it is possible to accurately measure the quantity of light while eliminating an influence of washing, and to perform a real-time measurement during the hybridization.

Next, a nucleic acid sequence measurement device will be described.

The nucleic acid sequence measurement device has the device for nucleic acid sequence measurement and a fluorescence-reading apparatus that measures the amount of fluorescence of the fluorescent molecule emitted from the device for nucleic acid sequence measurement.

Figure 5:
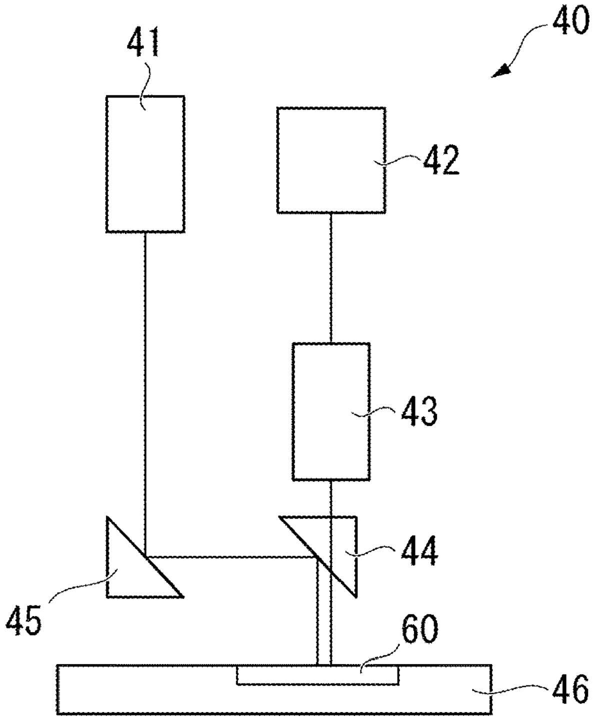
FIG. 5 is a view showing a configuration example of a nucleic acid sequence detection device.

FIG. 5 is an example of a configuration view showing the nucleic acid sequence measurement device. In order to acquire images before and after the binding of the target RNA 30 and the fluorescent probe 10, in a device 60 for nucleic acid sequence measurement in the nucleic acid sequence measurement device, an image before the binding is acquired, and then the temperature of the solid-phase surface of the device 60 for nucleic acid sequence measurement is raised by a temperature control stage 46 to allow the binding reaction to proceed and then lowered to room temperature again, in which state an image after the binding is acquired.

In order to accelerate the binding of the target RNA 30 and the fluorescent probe 10, it is preferable that the temperature control stage 46 have a function of shaking or stirring by rotation of the device for nucleic acid sequence measurement, a vortex mixer, and the like during the reaction between the target RNA 30 and the fluorescent probe 10.

In an optical system of a fluorescence-reading apparatus 40, laser light emitted from a laser light source 41 is reflected by a dichroic mirror 44 through a mirror 45 and the solid phase of the device for nucleic acid sequence measurement is irradiated with the laser light. The irradiated light serves as excitation light 33 for the fluorescent molecules 11 on the solid-phase surface of the device 60 for nucleic acid sequence measurement, and the fluorescent molecules 11 are put into an excited state to cause the fluorescent molecules 11 to emit fluorescence 34.

The fluorescence emitted from the solid-phase surface of the device 60 for nucleic acid sequence measurement is transmitted through the dichroic mirror 44, and passes through an imaging optical system 43, and thus, a fluorescent image on a detection element of a CCD camera 42 is formed and detected. Here, for the purpose of preventing the excitation light 33 from leaking into the fluorescence 34, a band-pass filter matched to an excitation light wavelength may be installed on the excitation light 33 side and a band-pass filter matched to a fluorescence wavelength to be detected may also be installed on the fluorescence 34 side.

For the fluorescent images obtained by the nucleic acid sequence measurement device, the images before and after the binding of the target RNA 30 and the fluorescent probe 10 in the same spot can be acquired. Therefore, there is no influence of variations in quantity of light between the solid phases and between the spots. In addition, the variation quantity of fluorescence can be calculated from the fluorescent images before and after the binding reaction, and the number of molecules that have undergone the binding reaction can be calculated. For the calculation of the variation quantity of the fluorescence, an average quantity of light in all spots may be used, or the variation quantity of fluorescence for each pixel of the spot image may also be used.

The nucleic acid sequence measurement device may be provided with a computer that controls the CCD camera 42, an arithmetic device that calculates a quantity of light of the image, and a recording apparatus that stores the image, the quantity of light, and the like.

In the nucleic acid sequence measurement device, in order to detect fluorescence from the surface opposite to an immobilized surface of the detection spot on the solid-phase surface, a fluorescence microscope, a confocal microscope, an evanescent fluorescence detection apparatus, a thin-film oblique illumination microscope, a sheet illumination microscope, a structured illumination microscope, a multiphoton excitation microscope, or the like can be used.

The scope of application of the present invention is not intended to be limited to the embodiments. The present invention can be widely applied to a nucleic acid sequence measurement method for measuring a target RNA having a specific nucleic acid sequence included in a sample by hybridization.

EXAMPLES

Hereinafter, the present invention will be described in more detail with reference to Examples, but is not limited to Examples.

(Experimental Example 1) RNA Extraction from *Staphylococcus Aureus*

*Staphylococcus aureus* (*S. aureus*, NBRC100910) was cultured in an SCD medium for 1 day, and 1 mL of the obtained culture solution was centrifuged at 5,000×g to remove the supernatant, thereby obtaining cells. The obtained cells were suspended in 2.50 μL of a lysis solution (composition: 50 mM Tris-HCl buffer solution (pH 8.0), 0.1% SDS), stored in a container, sealed, and heated at a temperature of 140° C. or 160° C. for 45 seconds to obtain an RNA extract.

2 μL of DNase (trade name: Recombinant DNase 1 (RNase-free); manufactured by Takara Bio Inc.; concentration 5 U/μt) was added to the obtained RNA extract and incubated at 37° C. for 10 to 30 minutes to decompose and remove DNA, and then an RNA fragment length was confirmed by electrophoresis. The results of performing the heating at 140° C. and the results of performing the heating at 160° C. are each shown in FIGS. 6 and 7.

Figure 6:
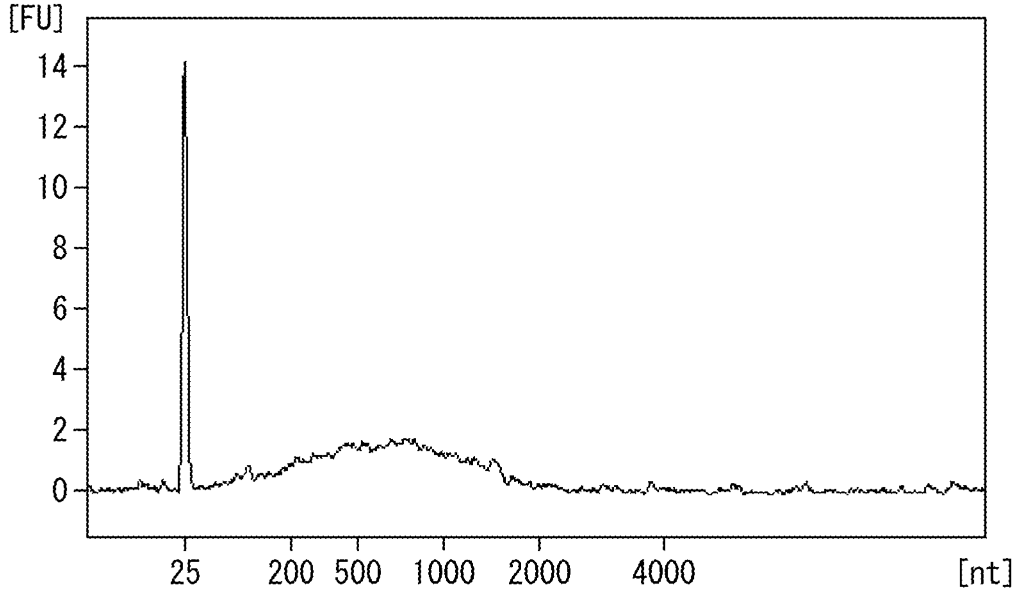
FIG. 6 is a view confirming the fragment length of an RNA fragment obtained by extracting an RNA by performing heating at 140° C. by electrophoresis in Experimental Example 1.
Figure 7:
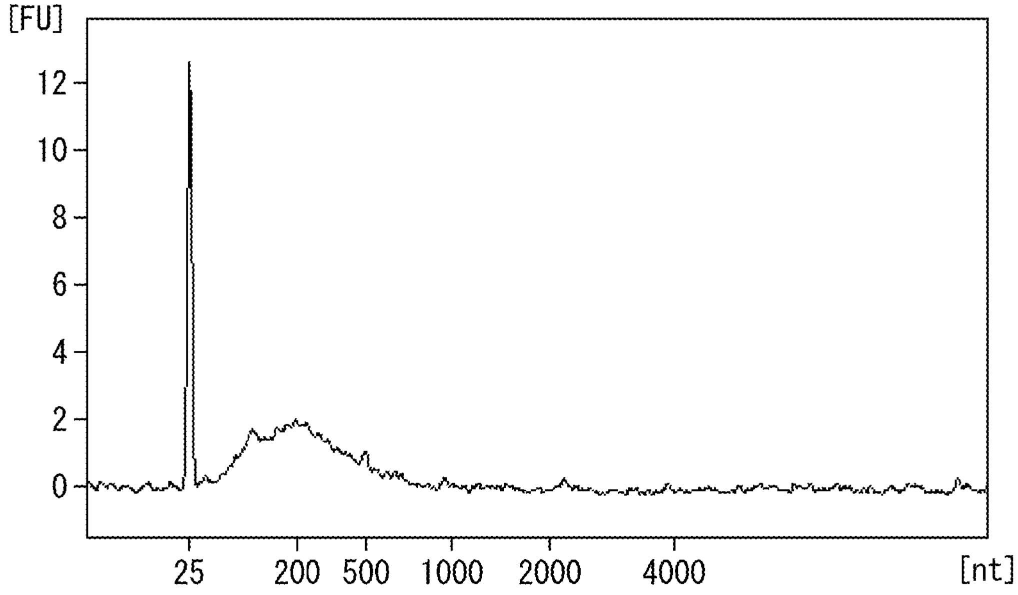
FIG. 7 is a view confirming the fragment length of an RNA fragment obtained by extracting an RNA by performing heating at 160° C. by electrophoresis in Experimental Example 1.

As shown in FIG. 6, it was confirmed that by heating at 140° C., a uniform fragmentation treatment into chain lengths suitable for hybridization is performed. In addition, as shown in FIG. 7, it was confirmed that by heating at 160° C., a fragmentation into shorter chain lengths can be performed and the hybridization efficiency can be further improved.

(Experimental Example 2) Detection of RNA Extracted from *Escherichia coli* by Device for Nucleic Acid Sequence Measurement

*Escherichia coli* (NBRC3972) was cultured in an SCD medium for 1 day, and 1 mL of the culture solution was centrifuged at 5,000×g to remove the supernatant, thereby obtaining cells. The obtained cells were suspended in 2.50 μL of a lysis solution (composition: 50 mM Tris-HCl buffer solution (pH 8.0), 0.1% SDS), stored in a container, sealed, and heated at a temperature of 140° C. for 45 seconds to obtain an RNA extract.

5 μL (final concentration: 500 μg/mL) of a proteinase K (Proteinase K, manufactured by Takara Bio Inc.) was added to the obtained RNA extract and incubated at 37° C. for 15 minutes.

Next, an SSC buffer solution was added thereto to provide a 5-fold diluted final concentration, and supplied to a microarray on which fluorescent probes capable of detecting *Escherichia coli* were immobilized. The microarray was incubated at 60° C. for 3 hours and the quantity of spot light from the microarray was measured by a fluorescence-reading apparatus. The results are shown in FIG. 8.

Figure 8:
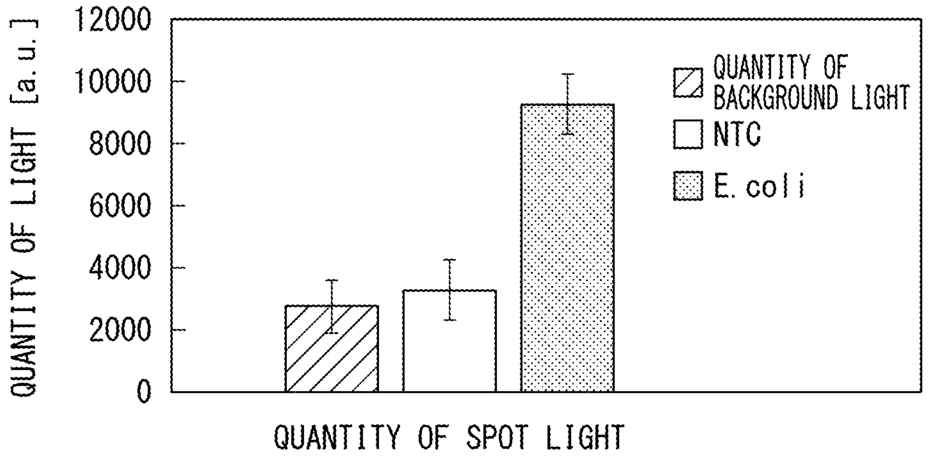
FIG. 8 is a graph showing the measured quantity of spot light emitted by a substrate onto which a fluorescent molecule has been dropped in a case where a proteolytic enzyme has been added to cause a reaction in Experimental Example 2.
Figure 9:
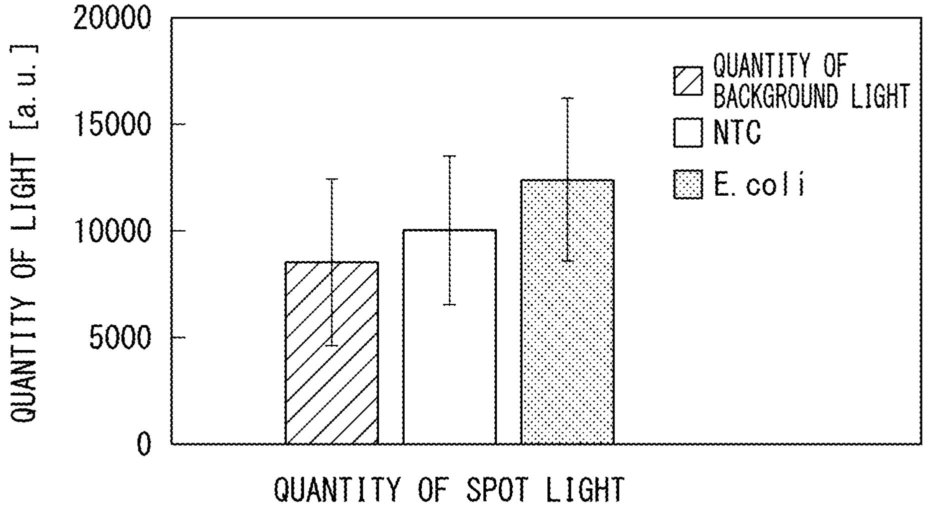
FIG. 9 is a graph showing the measured quantity of spot light emitted by a substrate onto which a fluorescent molecule has been dropped in a case where no proteolytic enzyme has been added in Experimental Example 2.

As a control, the RNA extract obtained above without addition of a proteinase K was supplied to the microarray in the same manner, the quantity of spot light was measured with a fluorescence-reading apparatus, and the results are shown in FIG. 9. In FIGS. 8 and 9, NTC shows the results of subjecting a sample solution including no target *Escherichia coli* to a microarray.

As shown in FIG. 8, in a case where the proteinase K was added to the RNA extract, the background light in a case where the target RNA was not present was low, and the increase in quantity of the spot light in a case where the target RNA was present was high. On the other hand, as shown in FIG. 9, in a case where the proteinase K was not added to the RNA extract, the background light in a case where the target RNA was not present was high, and the increase in quantity of the spot light in a case where the target RNA was present was low.

From the results above, it was confirmed that by adding a proteolytic enzyme to the RNA extract, the background light of the microarray is lowered and the light quantity in a case where the target RNA is present is increased, thus making it possible to detect the RNA from the cell extract with high accuracy.

REFERENCE SIGNS LIST

10: Fluorescent probe
11: Fluorescent molecule
12: X Part (binding part)
13: Detection sequence (detection part)
14: Linker (proximal end)
20: Quenching probe
21: Quenching molecule
22: Y Part (binding part)
23: Detection sequence (detection part)
24: Linker (proximal end)
30: Target RNA
60: Device for nucleic acid sequence measurement
40: Fluorescence-reading apparatus
41: Laser light source
42: CCD camera
43: Imaging optical system
44: Dichroic mirror
45: Mirror
46: Temperature control stage
100: Solid-phase surface

The invention claimed is:

1. A nucleic acid sequence measurement method for measuring a target RNA having a specific nucleic acid sequence included in a cell suspension by hybridization, comprising:

a step of heating the cell suspension at 100° C. to 200° C. in a pressurized state to obtain an RNA extract from which the RNA has been extracted;

a step of adding a proteolytic enzyme decomposing the cell-derived contaminant protein included in the RNA extract to the RNA extract from which the RNA has been extracted to cause the RNA extract to be reacted, thereby preparing a sample solution;

a step of supplying the sample solution to a device for nucleic acid sequence measurement, the device being equipped with a fluorescent probe that hybridizes with the target RNA;

a step of subjecting the target RNA and the fluorescent probe to a hybridization reaction; and a step of measuring fluorescence from the device for nucleic acid sequence measurement.

2. The nucleic acid sequence measurement method according to claim 1, wherein in the step of measuring the fluorescence, the fluorescence from the device for nucleic acid sequence measurement is measured without washing the sample solution supplied to the device for nucleic acid sequence measurement.

3. The nucleic acid sequence measurement method according to claim 1, wherein in the step of obtaining the RNA extract, the cell suspension is heated in a sealed container.

4. The nucleic acid sequence measurement method according to any one of claim 1, wherein the proteolytic enzyme is a proteinase K.

5. The nucleic acid sequence measurement method according to any one of claim 1, wherein the device for nucleic acid sequence measurement is equipped with a fluorescent probe having a binding part and a proximal end, and having a fluorescent molecule attached to a distal end or an intermediate position, a quenching probe having a binding part and a proximal end, and having a quenching molecule attached to a position near the fluorescent molecule of the fluorescent probe in a case where the quenching probe binds to the fluorescent probe, and a substrate having a solid-phase surface on which the proximal end of each of the fluorescent probe and the quenching probe is immobilized, wherein the binding part of the fluorescent probe and the binding part of the quenching probe have sequences complementary to each other, at least one of the fluorescent probe and the quenching probe has a detection part having a sequence complementary to a nucleic acid sequence of the target RNA, in a case where a hybridization between the target RNA and the detection part does not occur, binding between the binding part of the fluorescent probe and the binding part of the quenching probe is maintained, and fluorescence exhibited by the fluorescent molecule is consequently quenched by the quenching molecule approaching the fluorescent molecule, and in a case where the hybridization between the target RNA and the detection part occurs, the binding between the binding part of the fluorescent probe and the binding part of the quenching probe is dissociated consequently, and the proximal end of each of the fluorescent probe and the quenching probe is immobilized on the solid-phase surface to cause a positional relationship so that the fluorescent molecule separated from the quenching molecule exhibits fluorescence.

* * * * *